United States Patent [19]

Kanner

[11] Patent Number: 4,996,027

[45] Date of Patent: Feb. 26, 1991

[54] CONTACT LENS CASE HAVING PRESSURE VENTING GASKET

[75] Inventor: Rowland W. Kanner, Guntersville, Ala.

[73] Assignee: Ciba Vision Corporation, Atlanta, Ga.

[21] Appl. No.: 334,940

[22] Filed: Apr. 7, 1989

[51] Int. Cl.$^5$ .......................... A61J 1/00; G05G 15/00
[52] U.S. Cl. ..................................... 422/113; 206/5.1; 220/209; 422/117; 422/119; 422/297; 422/300; 422/305
[58] Field of Search ............... 422/113, 117, 119, 297, 422/300, 305; 206/5.1; 220/209

[56] References Cited

U.S. PATENT DOCUMENTS

| 3,173,571 | 3/1965 | Cserny et al. | 220/208 |
|---|---|---|---|
| 3,770,113 | 11/1973 | Thomas . | |
| 3,949,934 | 4/1976 | Goglio | 220/208 |
| 4,011,941 | 3/1977 | Parsons . | |
| 4,136,796 | 1/1979 | Dubois et al. . | |
| 4,197,097 | 4/1980 | Margorien et al. . | |
| 4,231,489 | 11/1980 | Malone | 220/367 |
| 4,301,629 | 11/1981 | Farr | 52/99 |
| 4,396,583 | 8/1983 | Le Boeuf . | |
| 4,457,327 | 7/1984 | Pepper | 422/310 |
| 4,469,237 | 9/1984 | Zerdian et al. | 220/209 |
| 4,512,771 | 4/1985 | Norton . | |
| 4,582,638 | 4/1986 | Homer et al. | 422/159 X |
| 4,637,919 | 1/1987 | Ryder et al. | 422/300 |
| 4,750,610 | 6/1988 | Ryder | 206/5.1 |
| 4,882,128 | 11/1989 | Hukvari et al. | 422/242 X |

Primary Examiner—Robert J. Warden
Assistant Examiner—Jill Johnston
Attorney, Agent, or Firm—R. A. Giangiorgi

[57] ABSTRACT

An appliance for containing and venting fluid, typically for disinfecting contact lenses, includes a container body which has an access opening and a removable closure for the opening. A gasket is seated to form a normally liquid-tight seal between the container body and the closure, and the gasket means has a composition which is sufficiently resilient to at least partially deflect and unseat from the container body upon exertion against the gasket of elevated gas pressure developed within the container, for example, during a disinfection process. The pressurized gas can then be vented past the unseated gasket which forms a vent passageway between the closure and the container body, after which venting the gasket redeflects to reseat and seal against the container body to prevent any subsequent leakage of fluid from the container body. As a result, the gasket serves not only as a closue seal, but also as a one-way check value for release of pressure, for example, during the disinfection process so that the alternative sealing and venting by the gasket are performed repeatedly.

20 Claims, 1 Drawing Sheet

CONTACT LENS CASE HAVING PRESSURE VENTING GASKET

BACKGROUND OF THE INVENTION

This invention relates to container appliances for chemical sterilization of small articles such as soft contact lenses, and more particularly, relates to pressure relief venting of such appliances.

In recent years, a disinfection treatment, particularly for soft contact lenses, has been developed in which the lenses are immersed in a solution of hydrogen peroxide which is catalytically decomposed to liberate disinfecting oxygen gas. As a result, the liberated oxygen produces a pressure increase within the disinfecting vessel which accordingly must be vented to the ambience. In U.S. Pat. No. 4,011,941 a contact lens sterilization container is described for use with hydrogen peroxide in which the described sterilization container includes a gasket to provide a water-proof seal between the cylindrical container body and removable cap on the container. The cap is provided with a complex configuration of oxygen-venting passageways leading to a venting groove formed in the upper part of the cap. An elastic O-ring fits into the vent groove, and as the pressure of the oxygen increases during the disinfection process within the container, the seal formed by the 0-ring acts a pressure relief valve to vent the oxygen. The disadvantages in molding the complex system of vent passageways in the cap are eliminated in the lens container and venting gasket in accordance with the present invention.

SUMMARY OF THE INVENTION

In accordance with the present invention, an appliance for containing and venting fluid, typically for disinfecting contact lenses, includes a container body which has an access opening and a removable closure for the opening. A gasket is seated to form a normally liquid-tight seal between the container body and the closure, and the gasket means has a composition which is sufficiently resilient to at least partially deflect and unseat from the container body upon exertion against the gasket of elevated gas pressure developed within the container, for example, during a disinfection process. The pressurized gas can then be vented past the unseated gasket which forms a vent passageway between the closure and the container body, after which venting the gasket redeflects to reseat and seal against the container body to prevent any subsequent leakage of fluid from the container body. As a result, the gasket serves not only as a closure seal, but also as a one-way check valve for release of pressure, for example, during the disinfection process so that the alternative sealing and venting by the gasket are performed repeatedly.

In a preferred embodiment of the appliance employed for disinfecting soft contact lenses or the like immersed in disinfecting solution within the container body, the gasket is carried on a removable cap so that the gasket normally seats against the peripheral rim formed on an opening end of the container body. The gasket is preferably fabricated from a plastic such as olefin polymer which can be foamed so that it has a closed cell foam structure which promotes the capacity of the gasket to withstand increased local deformation in order to vent the excessive gas pressure at the interface with the opening rim of the container body. A particularly preferred gasket structure is fabricated from cross-linked polyethylene having a closed cell foam structure and a continuous, protective skin at the sealing surfaces of the gasket.

DETAILED DESCRIPTION OF THE ILLUSTRATED EMBODIMENT

Figure 2:
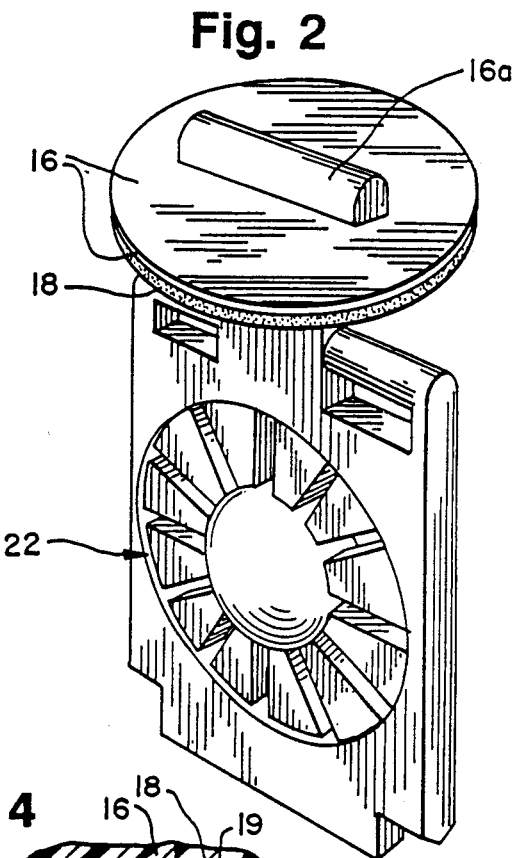
FIG. 2 is an enlarged, perspective view of a depending portion of the cap shown in FIG. 1 on which a venting gasket is mounted.
Figure 1:
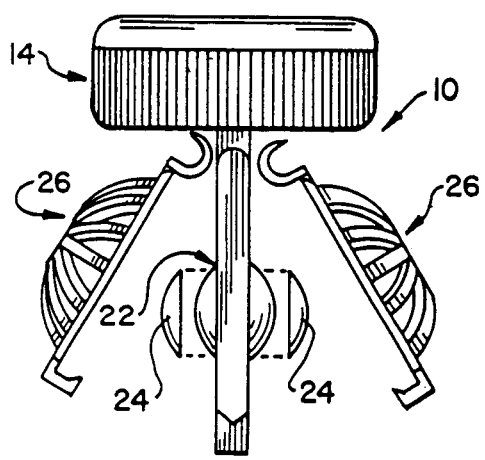
FIG. 1 is an exploded, partial elevational view of a lens disinfecting appliance employed in one embodiment of the invention.
Figure 1:
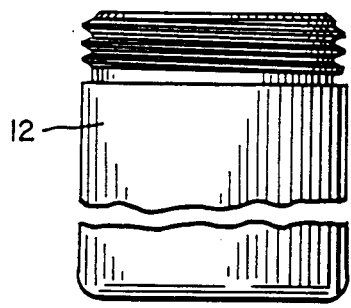
Figure 3:
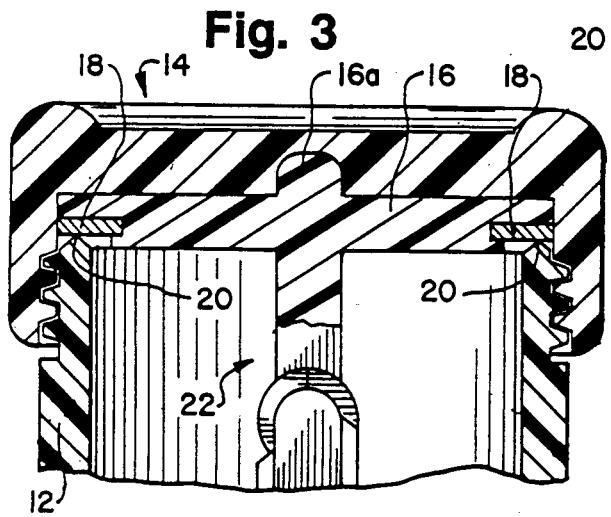
FIG. 3 is a sectional view of the assembled cap and container body as shown in FIG. 1 and illustrating the normally seated position of the gasket.

Referring now in more detail to FIGS. 1, 2 and 3, one embodiment of the contact lens disinfecting appliance in accordance with the present invention is generally designated by reference character 10. The appliance 10 includes a generally cylindrical container body 12 having a threaded end opening for receiving a removable screw cap 14. As best shown in FIGS. 2 and 3, the cap 14 includes a closure disc 16 having a upwardly projecting tongue 16a which is secured in a mating mortise, for example, by sonic welding. The closure disc or flange 16 has a grooved periphery within which an annular gasket 18 is secured. The gasket 18 normally seals against the end rim 20 at the opening of the container body 12. The flange 16 forms the upper part of a depending lens-supporting frame 22 which projects downwardly into the cavity within the cylindrical container body 12 when the cap 14 is mounted thereon. A pair of contact lenses 24 are enclosed and supported by the frame 22 and respective pivotal baskets 26 as more fully described in U.S. Pat. No. 4,750,610, the text of which is incorporated by reference herein. The baskets 26 are perforated to allow passage of the disinfecting liquid such as hydrogen peroxide solution within which the lenses 24 are immersed.

Figure 4:
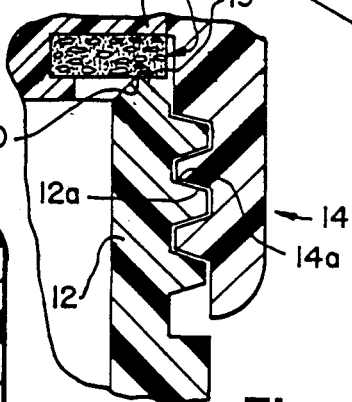
FIG. 4 is an enlarged, partial sectional view broken away from FIG. 3, further illustrating the seated gasket.
Figure 5:
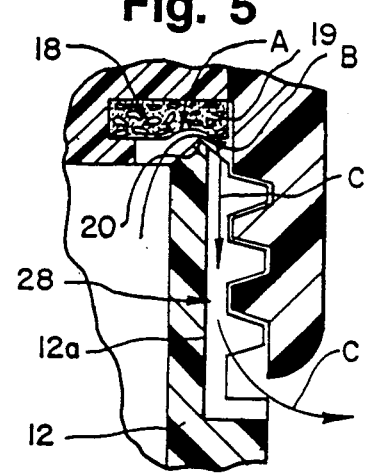
FIG. 5 is a sectional view similar to FIG. 4 illustrating local deformation and unseating of the gasket to enable venting of the pressurized gas from the container body.

In the disinfecting process, the hydrogen peroxide solution is poured into the container body 12 and the cap 14 is threaded thereon to seal the gasket 18 against the rim 20 as shown in FIG. 4, thereby immersing the lenses 24 within the solution. A catalytic element (not shown) initiates decomposition of the hydrogen peroxide solution and as the disinfecting reaction proceeds, the liberated oxygen exerts progressively elevated pressure within the container body 12. When the pressure reaches an excessive level requiring venting, exertion of the pressure causes local compression or deformation indicated by arrow A in FIG. 5, of the gasket 18 whereat the gasket unseats from the rim 20 to provide a vent passageway B through which the pressurized oxygen is released to ambience as indicated by arrow C. In FIG. 5, the threads 12a of the container body 12 are fabricated to include a generally vertically oriented slot 28 in order to provide an enlarged vent conduit for pressurized oxygen flow from the passageway B provided by the unseated portion A of the gasket 18. Alternatively, as illustrated in FIG. 4, the cap threads 14a and container body threads 12a can be loosely threaded together to form sufficient clearance space therebetween to provide conduit passageway for flow of pressurized oxygen therethrough when the oxygen is vented by the gasket 18 in the manner shown in FIG. 5.

Once sufficient pressurized oxygen has been vented from the container body 12 to reduce the gas pressure exerted upon the gasket 18 to a level allowing resilient relaxation of the local deformation A and reseating of the gasket 18 on the rim 20, liquid-tight, sterile seal is thereby reestablished to prevent any liquid leakage of the remaining solution from the container body.

In order to promote the capacity of the gasket to withstand reversible, increased local deformation with the excessive gas pressure at the interface with the end rim 20 as shown in FIG. 5, beyond the normal local compression to provide the liquid-tight seal as shown in FIG. 4, the gasket is preferably fabricated from plastic such as an olefin polymer which can be foamed so that it has a closed cell foam structure. In such structure, the cells 19 which are already under mild local mechanical loading due to the normal liquid-tight sealing compression of the cap closure, withstand sufficient additional resilient deformation by the gas pressure produced within the container body during the disinfection reaction, and once the excessive gas pressure has been vented, the decompression of the cells enables resilient reseating of the gasket against the rim to reseal in liquid-tight closure. As a result, the gasket serves not only as a closure seal, but also as a one-way check valve for release of the elevated gas pressure during disinfection, so that the alternative sealing and venting by the gasket are performed repeatedly.

Figure 6:
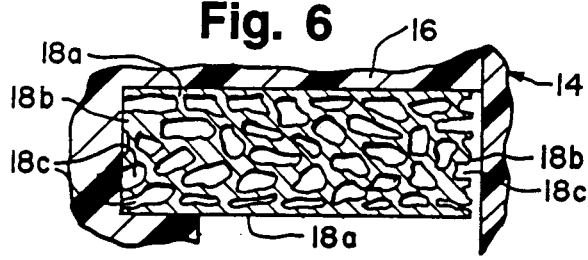
FIG. 6 is a sectional view of the gasket shown in FIGS. 3 and 4, further illustrating the internal structure of the gasket.

As shown in FIG. 6, the gasket structure preferably includes a continuous "skin" 18a of plastic, at least at the opposing sealing surfaces in order to provide the gasket with tough and durable sealing surfaces which must withstand reversible deformation in a repeated manner. The side edges 18b of the gasket can be discontinuous, for example, when the gasket is die stamped, and the closed cell structure of the gasket prevents any extensive migration of liquid which might enter the severed cells 18c adjacent the discontinuous gasket edges 18b. Suitable plastics which can be foamed and cross-linked include for example, olefin polymers such as polyethylene and polypropylene, which can additionally provide high surface tension to repel aqueous solutions and promote the normal, water-tight seal and closure of the container body by the gasket.

In addition to employment in contact lens disinfecting appliances, the described gasket materials can be used in similar applications wherein elevated gaseous pressure must be relieved and the gasket serves combined sealing and venting functions. By extension, such a gasket structure can be employed where an initially evacuated vessel is maintained under seal by the gasket followed by introduction into the container of liquid or gas under pressure, and thereafter the gasket can provide resealable venting for elevated pressure developed within the container such as in a sterilization process.

In light of the foregoing description of the embodied appliances of the invention, it will be evident to those skilled in the design of such appliances that various aspects may be modified without departing from the invention. As such, the scope of the invention is not limited by the particular embodiment illustrated and described herein and is defined by the appended claims and equivalence thereof.

What is claimed is:

1. An appliance for disinfecting contact lenses or the like immersed within a disinfecting solution which liberates gas during the disinfecting process, said appliance comprising: a container body including an opening at one end thereof; a removable cap means for closing said opening; and self-reseating, unitary gasket means disposed to form a normally liquid tight seal between said container body and an engaged surface of said cap means, wherein said self-reseating, unitary gasket means comprises a composition sufficiently resilient to at least partially deflect and unseat from said container body while said cap means remains stationary upon said container body upon exertion against said self-reseating, unitary gasket means of elevated pressure by gas liberated within said container body during said disinfection process so that said pressurized gas is vented past said unseated gasket means which forms a vent passageway between said cap means and container body, after which venting said self-reseating, unitary gasket means redeflects to reseat and seal against said container body in order to prevent any subsequent leakage of said solution therefrom.

2. An appliance according to claim 1 wherein said self-reseating, unitary gasket means is mounted on said removable cap means for providing said normal seal against said opening end of said container body.

3. An appliance according to claim 2 wherein said cap means further comprises lens holder means for supporting contact lens within said container body.

4. An appliance according to claim 2 wherein said cap means further comprises closure flange means on which said self-reseating, unitary gasket means is carried for said normal seating against a peripheral rim formed on said opening end of said container body.

5. An appliance according to claim 4 wherein said gasket means is fabricated in annular configuration for alignment with said peripheral rim.

6. An appliance according to claim 1 wherein said self-reseating, unitary gasket means composition comprises a plastic having a closed cell foam structure.

7. An appliance according to claim 6 wherein said plastic comprises an olefin polymer.

8. An appliance according to claim 7 wherein said olefin polymer is cross-linked.

9. An appliance according to claim 7 wherein said olefin polymer comprises polypropylene.

10. An appliance according to claim 7 wherein said olefin polymer comprises polyethylene.

11. An appliance according to claim 7 wherein said olefin polymer comprises cross-linked polyethylene.

12. An appliance for disinfecting contact lenses or the like immersed within a disinfecting solution which liberates gas during the disinfecting process, said appliance comprising: a container body including an opening at one end thereof; a removable cap means for closing said opening; and gasket means disposed to form a normally liquid tight seal between said container body and cap means, wherein said gasket means has a composition comprising cross-linked polyethylene having a closed cell foam structure and wherein said gasket means further comprises at least one surface layer of continuous polyethylene without foam cells, such that said gasket means is sufficiently resilient to at least partially deflect and unseat from said container body upon exertion against said gasket means of elevated pressure by gas liberated within said container body during said disinfection process so that said pressurized gas is vented past said unseated gasket means which forms a vent passageway between said cap means and container body, after which venting said gasket means redeflects to reseat against said container body in order to prevent any subsequent leakage of said solution therefrom.

13. An appliance for containing and venting fluid, comprising: a container body including an opening; closure means for closing said opening; an self-reseating, unitary gasket means disposed to form a normally tight seal between said container body and said closure means wherein said self-reseating, unitary gasket means comprises a composition sufficiently resilient to at least partially unseat from said container body while an engaged surface of said cap means remains stationary upon said container body upon exertion against said self-reseating, unitary gasket means of fluid pressure within said container body, so that said pressurized fluid is vented past said unseated gasket means which forms a vent passageway between said closure means and said container body, after which said self-reseating, unitary gasket means deflects to reseat and seal against said container body in order to prevent any subsequent leakage of fluid therefrom.

14. An appliance according to claim 13 wherein said self-reseating, unitary gasket means composition comprises a plastic having a closed cell foam structure.

15. An appliance according to claim 14 wherein said plastic comprises an olefin polymer.

16. An appliance according to claim 15 wherein said olefin polymer is cross-linked.

17. An appliance according to claim 15 wherein said olefin polymer comprises polypropylene.

18. An appliance according to claim 15 wherein said olefin polymer comprises polyethylene.

19. An appliance according to claim 15 wherein said olefin polymer comprises cross-linked polyethylene.

20. An appliance for containing and venting fluid, comprising: a container body including an opening; closure means for closing said opening; and gasket means disposed to form a normally tight seal between said container body and said closure means wherein said gasket means has a composition comprising cross-linked polyethylene having a closed cell foam structure and wherein said gasket means further comprises at least one surface layer of continuous polyethylene without foam cells, such that said gasket means is sufficiently resilient to at least partially unseat from said container body upon exertion against said gasket means of fluid pressure within said container body, so that said pressurized fluid is vented past said unseated gasket means which forms a vent passageway between said closure means and said container body, after which said gasket means deflects to reseat against said container body in order to prevent any subsequent leakage of fluid therefrom.

* * * * *